United States Patent [19]

Li et al.

[11] Patent Number: 5,263,984
[45] Date of Patent: Nov. 23, 1993

[54] PROSTHETIC LIGAMENTS

[75] Inventors: Shu-Tung Li, Oakland, N.J.; Kevin R. Stone, Mill Valley, Calif.

[73] Assignee: ReGen Biologics, Inc., San Francisco, Calif.

[21] Appl. No.: 872,636

[22] Filed: Apr. 22, 1992

Related U.S. Application Data

[60] Continuation-in-part of Ser. No. 582,516, Sep. 13, 1990, Pat. No. 5,116,374, which is a division of Ser. No. 317,951, Mar. 2, 1989, Pat. No. 5,007,934, which is a continuation-in-part of Ser. No. 75,352, Jul. 20, 1987, Pat. No. 4,880,429.

[51] Int. Cl.⁵ ............................................. A61F 2/08
[52] U.S. Cl. ........................................ 623/15; 623/66
[58] Field of Search ..................... 623/1, 2, 11, 12, 15, 623/17, 16, 18, 20, 66; 128/DIG. 8

[56] References Cited

U.S. PATENT DOCUMENTS

| | | |
|---|---|---|
| 3,443,261 | 5/1969 | Battista et al. . |
| 3,551,560 | 12/1970 | Thiele . |
| 3,885,638 | 12/1974 | Pilliar . |
| 4,000,525 | 1/1977 | Klawitter et al. . |
| 4,055,862 | 11/1977 | Farling . |
| 4,060,081 | 11/1977 | Yannas et al. . |
| 4,064,567 | 12/1977 | Burstein et al. . |
| 4,085,466 | 4/1978 | Goodfellow et al. . |
| 4,116,898 | 9/1978 | Dudley et al. . |
| 4,280,954 | 7/1981 | Yannas et al. . |
| 4,291,013 | 9/1981 | Wahlig et al. . |
| 4,334,193 | 8/1982 | Kenny . |
| 4,350,629 | 9/1982 | Yannas et al. . |
| 4,351,069 | 9/1982 | Ballintyn et al. . |
| 4,378,224 | 3/1983 | Nimni et al. . |
| 4,385,404 | 5/1983 | Sully et al. . |
| 4,400,833 | 8/1983 | Kurland . |
| 4,418,691 | 12/1983 | Yannas et al. . |
| 4,448,718 | 5/1984 | Yannas et al. . |
| 4,458,678 | 7/1984 | Yannas et al. . |
| 4,472,840 | 9/1984 | Jefferies . |
| 4,502,161 | 3/1985 | Wall . |

(List continued on next page.)

FOREIGN PATENT DOCUMENTS

| | | |
|---|---|---|
| 1170001 | 7/1981 | Canada . |
| 0277678 | 1/1985 | European Pat. Off. . |
| 0260970 | 9/1987 | European Pat. Off. . |
| 0282091 | 3/1988 | European Pat. Off. . |
| 2510394 | 7/1981 | France . |
| 2596641 | 4/1986 | France . |
| 2651994 | 9/1989 | France . |
| WO83/03536 | 10/1983 | PCT Int'l Appl. . |
| WO88/06872 | 9/1988 | PCT Int'l Appl. . |
| 1515963 | 7/1975 | United Kingdom . |
| 2164343 | 7/1985 | United Kingdom . |

OTHER PUBLICATIONS

Teitge (1988) in *The Crucial Ligament* (Feagin, ed.) New York, Churchill-Livingston, pp. 529-534.
Jackson et al. (1990) *Am. J. Sports Med.* 18:1-10.
Noyes et al. (1990) *J. Bone Joint Surg.* 72-A:1125-1136.
Shino et al. (1990) *Am. J. Sports Med.* 18:457-465.
Johnson et al. (1992) *J. Bone Joint Surg.* 74-A:140-151.
Nyiles et al. (1983) *Trans. Am. Soc. Artif. Intern. Organs* 29:307-312.
Rovere et al. (1983) *Am. J. Sports Med.* 104:205.
Webster (1983) *Clin. Orthop.* 181:238.
Friedman et al. (1985) *Clin. Orthop.* 196:9.
Woods (1985) *Orthop. Clin. North Am.* 16:227.

(List continued on next page.)

*Primary Examiner*—David Isabella
*Attorney, Agent, or Firm*—Lahive & Cockfield

[57] ABSTRACT

Disclosed is a prosthetic ligament comprising a Plurality of substantially aligned, elongated filaments. Each filament is a dry, porous, volume matrix of biocompatible and bioresorbable fibrils, at least some of which are crosslinked. The fibrils are short segments of longer fibers of polymeric connective tissue components, or analogs thereof. Each filament establishes a bioresorbable scaffold adapted for ingrowth of ligament fibroblasts, the scaffold and the ingrown fibroblasts supporting natural ligament tensile forces. Also disclosed are methods of fabricating the prosthetic ligament, and methods of regenerating ligamentous tissue in vivo.

21 Claims, 4 Drawing Sheets

U.S. PATENT DOCUMENTS

| | | |
|---|---|---|
| 4,505,266 | 3/1985 | Yannas et al. |
| 4,542,539 | 9/1985 | Rowe, Jr. et al. |
| 4,544,516 | 11/1985 | Hughes et al. |
| 4,578,079 | 3/1986 | Ruoslahti et al. |
| 4,589,881 | 5/1986 | Pierschbacher et al. |
| 4,600,652 | 7/1986 | Solomon et al. |
| 4,614,794 | 9/1986 | Easton et al. |
| 4,627,853 | 12/1986 | Campbell et al. |
| 4,661,111 | 4/1987 | Ruoslahti et al. |
| 4,719,246 | 1/1988 | Murdoch et al. |
| 4,720,512 | 1/1988 | Hu et al. |
| 4,734,097 | 3/1988 | Tanabe et al. |
| 4,766,182 | 8/1988 | Murdoch et al. |
| 4,790,850 | 12/1988 | Dunn et al. |
| 4,800,219 | 1/1989 | Murdoch et al. |
| 4,801,299 | 1/1989 | Brendel et al. ............... 623/1 |
| 4,932,972 | 6/1990 | Dunn et al. |
| 4,963,146 | 10/1990 | Li |
| 5,067,962 | 11/1991 | Campbell et al. |
| 5,078,744 | 1/1992 | Chvapil |
| 5,078,745 | 1/1992 | Rhenter et al. |
| 5,092,887 | 3/1992 | Gendler |
| 5,092,894 | 3/1992 | Kenny |
| 5,171,273 | 12/1992 | Silver et al. ............... 623/13 |

OTHER PUBLICATIONS

Amiel et al. (1986) *Am. J. Sports Med.* 14:449–462.
Arnold, et al. (1979) *Am. J. Sports Med.* 7:305.
Bright, et al. (1981) *J. Pediatr. Orthop.* 1:13.
Minami et al. (1982) *Hand* 14:111.
Frank et al. (1983) *J. Orthopaed. Res.* 1:179–188.
Frank et al. (1983) *J. Sports Med.* 11:379–389.
McDaniel et al. (1983) *Clin. Orthop.* 172:158.

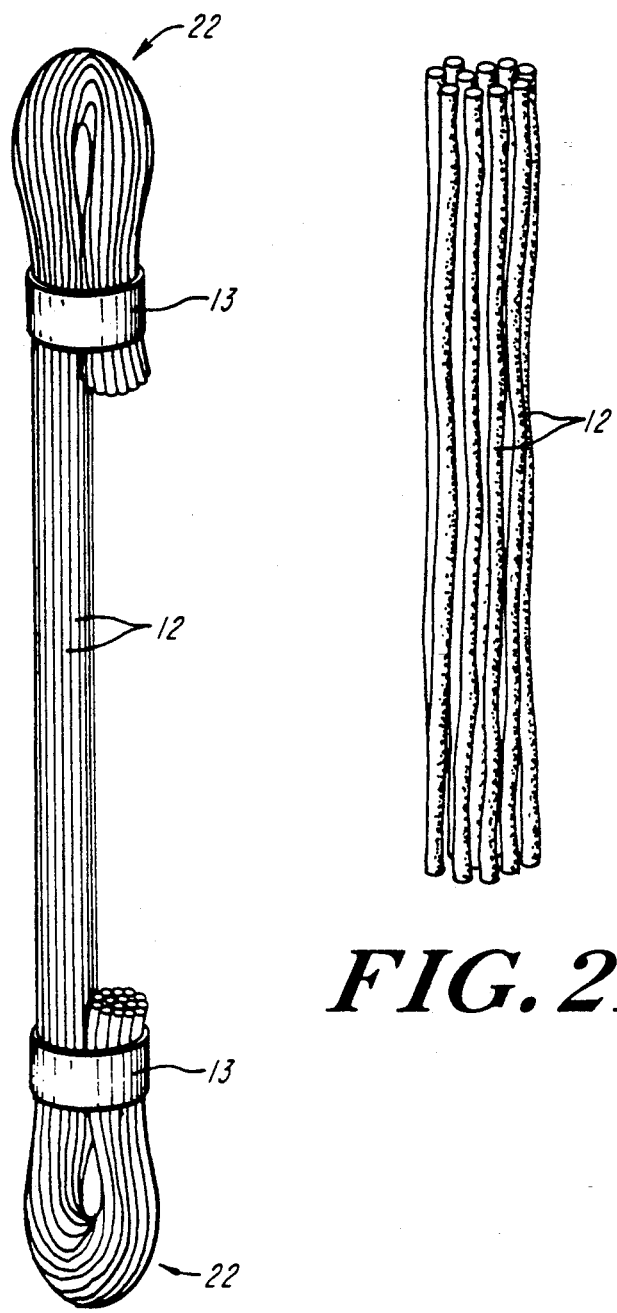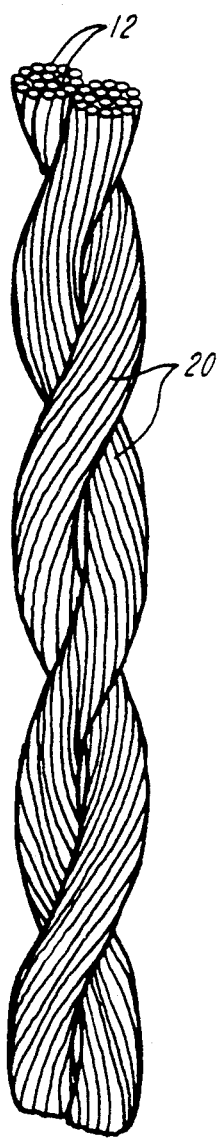
FIG. 2D
FIG. 2E
FIG. 2B

PROSTHETIC LIGAMENTS

REFERENCE TO RELATED APPLICATIONS

This application is a continuation-in-part of copending U.S. patent application Ser. No. 582,516 filed Sep. 13, 1990, now U.S. Pat. No. 5,116,374, which is a divisional of U.S. patent application Ser. No. 317,951, filed Mar. 2, 1989, now U.S. Pat. No. 5,007,934, issued Apr. 16, 1991, which is a continuation-in-part of U.S. patent application Ser. No. 075,352, filed Jul. 20, 1987, now U.S. Pat. No. 4,880,429, issued Nov. 14, 1989.

BACKGROUND OF THE INVENTION

The present invention is in the field of implantable medical devices and prostheses. More particularly, this invention is directed to devices useful as prosthetic ligaments and in vivo scaffolds for the regeneration of ligamentous tissue, and to methods of their fabrication and use.

Ligaments connect one bone to another usually where the bones form articulating joints in the human and animal species. The ligaments act in the joint as a mechanism for maintenance of joint stability, for guidance of joint motion, and for resistance to joint distraction forces. Without ligaments, the human and animal species would be unable to maintain the erect form. Injury to the ligaments results in either a normal physiological repair process, which can lead to resumption of normal joint mechanics, or to inadequate repair with loss of joint stability, abnormal joint motions, and occasionally to painful arthritis as a result of abnormal joint surface wear and tear. In general, ligaments that are outside of joints, and bathed in a rich vascular supply, have a good chance of healing normally after injury. Ligaments that are inside of joints, termed intra-articular ligaments, are generally bathed in synovial fluid, have a relatively poor blood supply, and heal poorly.

In the prior art, treatment of injured ligaments has generally been both by attempts to protect the ligament from further deforming stress and thereby to permit a normal physiological repair process to occur or to attempt a surgical repair with sutures, replacement, or excision (Johnson, R. J. et al. (1992) *J. Bone Joint Surg.* 74-A:140-151; Arnold et al. (1979) *Am. J. Sports Med.* 7:305; McDaniel et al. (1983) *Clin. Orthop.* 172:158; Rovere et al. (1983) *Am. J. Sports Med.* 104:205). With non-operative or operative repair, healing and regeneration of ligamentous tissue may occur. Generally, if the ligament is located intra-articularly, the repaired tissue is usually inferior to the original tissue and sometimes inadequate to withstand the normal joint forces. In view of the insufficiency of many primary repairs several previous attempts have been made to replace the ligamentous tissue with natural and artificial materials. Unfortunately, this also has resulted in significant problems related to those replacement materials.

In particular, replacement of ligaments in the prior art has been by autografting (Friedman et al. (1985) *Clin. Orthop.* 196:9), allografting (Webster (1983) *Clin. Orthop.* 181:238), xenografting (McMaster (1988) in *"Prosthetic Ligament Reconstruction of the Knee"* (Friedman and Ferkel, (eds.), W. B. Saunders, Philadelphia, pp. 96-100), or by using synthetic materials (Woods (1985) *Orthop. Clin. North Am.* 16:227). Autografting, or the substitution of the injured ligament with ones own tissue, is still the preferred modality (Amiel et al. (1986) *Am. J. Sports Med.* 14:449-462; Warren et al. (1990) *AAOS 57th Annual Meeting,* Anaheim, Calif, p. 84). Autografting alleviates the risk of transmission of diseases between donor and recipient, immunological complications, and complications from foreign body reactions. However, the weakening of the body part from which the substitution tissue is harvested, the extensive surgical procedures with both harvesting of the donor tissue and substituting the injured tissue, and the inadequate mechanical strength of the substituted tissues have prompted the search for alternative methods of repair.

Allografting, or the substitution of injured ligament with tissues from another person (either preserved live tissue or chemically processed tissue), has been practiced (Noyes et al. (1990) *J. Bone Joint Surg.* 72-A:1125-1136; Shine et al. (1990) *Am. Sports Med.* 18:457-465; Webster (1983) *Clin. Orthop.* 181:238; Bright et al. (1981) *J. Pediatr. Orthop.* 1:13). This approach has been only partially successful over the long term due primarily to the host's immunologic response to the graft, and to failures in the preservation and sterilization processes (Jackson et al. (1990) *Am. J. Sports Med.* 18:1-10; Minami et al. (1982) *Hand* 14:111). In addition, the risk of disease transmission is of particular concern for allografting (Prewett et al. (1991) *Orthop. Res. Soc.* 16:456).

Xenografting, or the substitution of the injured ligament with tissues from animal sources, has been tried. However, because of inadequate material processing leading to the presence of toxic and immunological substances in the graft, this method has met with minimal success (Teitge (1988) in *The Crucial Ligament,* (Feagin, ed.) New York, Churchill-Livingston, pp. 529-534).

Various synthetic polymers have been fabricated for ligament substitution, such as polypropylene, polyethylene terephthalate, carbon, polytetrafluroethylene (Claes et al. (1991) *Orthop. Res. Soc.* 16:598). Ligament substitution devices are intended to function as permanent implants, and thus are subjected to continuous intraarticular wear and tear. However, none of the present synthetic polymeric ligament devices has functioned successfully as a ligament substitute. Such devices have failed because of ligament rupture, joint particle reduction and resultant synovitis, abrasion of opposing joint surfaces, infection required extensive joint debridement and ligament removal, persistent effusion, and bony tunnel widening (Woods et al. (1991) *Am. J. Sports Med.* 19:48-55; Woods (1985) *Orthop. Clin. North Am.* 16:227). Thus, artificial materials are generally insufficiently durable or mechanically compatible to tolerate the repetitive joint loading, and have never been demonstrated to restore normal joint mechanics.

The concept of a resorbable template or scaffold for tissue repair and regeneration has received rigorous attention in recent years. Repair of tissues such as skin, nerve, and meniscus has been attempted using both the synthetic and natural resorbable polymers. For example, Yannas et al. (U.S. Pat. No. 4,060,081) fashioned endodermal implants out of glycosaminoglycans and natural collagen. Nyiles et al. (*Trans. Am. Soc. Artif. Intern. Organs* (1983) 29:307-312) reported the use of synthetic resorbable polyesters for peripheral nerve regeneration applications. Li (U.S. Pat. No. 4,963,146) used a porous, semipermeable, resorbable collagen conduit as a scaffold for nerve regeneration.

However, even with the foregoing technologies, which have been applied to the reconstruction of anatomical structures, a structure successful as a prosthetic ligament and constructed from totally resorbable materials, or analogs thereof, has not yet been developed. Therefore, what is needed is a prosthetic ligament including a scaffold composed of biocompatible materials which is soft, strong, resorbable, and which can support ligamentous growth.

Accordingly, it is an object of this invention to provide a ligament replacement or prosthesis which is biomechanically able to withstand normal joint forces and is able to function at those loads to protect the surrounding cartilage.

Another object is to provide a ligament replacement or prosthesis which is biomechanically able to provide joint stability.

Yet another object is to provide a resorbable prosthesis which acts as temporary in vivo scaffold for ligament fibroblast infiltration and ligament regeneration.

A further object is to provide a method for insertion and fixation of a ligament prosthesis.

Another object is to provide a method of regenerating ligamentous tissue in vivo.

Still a further object is to provide a method by which such prosthetic ligament can be fabricated.

SUMMARY OF THE INVENTION

The present invention provides a biocompatible and bioresorbable structure for implantation adjacent and into articulating joints which assumes the form and role of the ligament. This prosthetic ligament promotes and provides a scaffold for the regeneration of tissue having the physical characteristics of natural ligament tissue whereby the scaffold and the ingrown fibroblasts support natural ligament tensile forces.

The prosthetic ligament of the invention is a plurality of substantially aligned, elongated filaments substantially aligned in a mutually adjacent relationship. These filaments establish a bioresorbable scaffold adapted for ingrowth of ligament fibroblasts, and together with those ingrown cells, support natural ligament tensile forces.

Each filament is a dry, porous, volume matrix of biocompatible and bioresorbable fibrils, at least some of which are crosslinked. "Fibrils" as used herein are segments or short pieces of fibers of native polymeric connective tissue-type components, such as those obtained from human, animal tissues, plants, insects, or analogs thereof. Preferable connective tissue-type components include collagen, elastin, reticulin, cellulose, alginic acid, and chitosan, with the most preferable being collagen type I.

Some of the fibrils in the filament are connected via intramolecular and/or interfibrillar crosslinks. In one aspect of the invention, these crosslinks are formed by a chemical crosslinking reagent such as one selected from the group consisting of glutaraldehyde, formaldehyde, carbodiimides, hexamethylene diisocyanate, bisimidates, glyoxal, polyglycerol polyglycidyl ether and adipyl chloride. A preferred chemical agent is formaldehyde.

In some embodiments of the invention, the fibrils are randomly oriented throughout the matrix. In other forms, these fibrils are predominantly oriented along the axis of the filament.

A preferred prosthetic ligament also includes polysaccharide molecules interspersed with the fibrils. In various forms of the invention, these polysaccharides directly participate in covalent crosslinking formation with the fibrils, or interact with the fibrils mechanically in the form of entanglement or through interlocking mechanism, forming stable fibril-polysaccharide complexes. As such, these polysaccharides molecules provide lubrication, hydrophilicity, and strength to the prosthetic ligament. Preferably, these polysaccharide molecules have a molecular weight greater than 1000, and are selected from the group consisting of chondroitin 4-sulfate, chondroitin 6-sulfate, keratan, dermatan sulfate, haparan sulfate, heparin, hyaluronic acid, alginic acid, chitosan, cellulose, and mixtures thereof. These polysaccharides may be uniformly dispersed throughout the prosthetic ligament as individual molecules, or may be present in varying amounts in different regions of the structure.

The matrix includes about 75 to 100% natural and/or synthetic fibers and about 0 to 25% polysaccharide molecules by dry weight, the proportions of which may be constant throughout the structure or may be variable.

In one preferred embodiment of the invention, the prosthetic ligament is primarily a composite of two densities of filaments, with the more porous, or "low density" filament having a density of from about 0.05 to 0.4 g matrix/cm$^3$, and more preferable, from about 0.07 to 0.3 g matrix/cm$^3$, (where "g matrix/cm$^3$" is a unit connoting the number of grams in a cubic centimeter of the matrix), and the less porous, or "high density" filament has a density in the range of from about 1.0 to about 1.3 g matrix/cm$^3$.

In one embodiment, the prosthetic ligament has the shape of a filamentous braid with a loop at one end and a straight bundles of filaments at the other end to aid in insertion and fixation to bone. In another, a plurality of filaments are twisted together.

In yet another embodiment of the invention, the prosthetic ligament further comprises a mesh or membrane composed of a bioresorbable, biocompatible material which is attached to portions of the outer surface of the matrix. The mesh or membrane aids in the implantation of the prosthetic ligament into the joint by providing a temporary anchoring mechanism.

This invention also encompasses a method of fabricating a prosthetic ligament of the type described above. Generally, the method includes the following steps. A plurality of essentially pure fibers of a polymeric connective tissue component is provided and cut into a plurality of segments or fibrils which are shorter than the fibers. Cutting may be accomplished by mechanical disintegration, for example. The fibrils are then aggregated into a plurality of elongated filaments and contacted with a crosslinking reagent for a time sufficient to crosslink at least a portion of the fibrils within the filaments. The filaments are then aligned in a mutually adjacent relationship to form the prosthetic ligament. Polysaccharide molecules may be added to the fibrils before the aggregation step to form polysaccharide-containing prosthetic ligaments.

In one embodiment of the invention, the aggregation step is accomplished by providing a dispersion of fibrils; forming the dispersion into a filamentous shape; and drying it to form a filament. The forming step can include extruding the dispersion from a syringe into a coacervation bath of a high concentration neutral salt. Alternatively, the dispersion is placed into a mold form having a filamentous shape such that the fibrils are randomly or uniformly oriented throughout said dispersion in said mold form. Portions of the coacervated fibrils are freeze-dried to produce the low density filaments, and other portions are air dried to obtain the high density filaments. Both the low and high density filaments are crosslinked to increase the strength and in vivo stability of the prosthetic device.

In a preferred aspect of the invention, the crosslinking step is performed using chemical crosslinking reagents which form interfibrillar and intermolecular crosslinks. In other aspects of the invention, an additional crosslinking step is performed by subjecting the chemically crosslinked matrix to a dehydrothermal crosslinking procedure with heat and vacuum.

Further, the invention includes a method of regenerating ligamentous tissue in vivo. This method includes providing the prosthetic ligament of the invention and implanting it into a joint by known surgical procedures.

The invention will next be described in connection with certain illustrated embodiments. However, it should be clear that various modifications, additions, and deletions can be made without departing from the spirit or scope of the invention.

BRIEF DESCRIPTION OF THE DRAWINGS

The foregoing and other objects of this invention, the various features thereof, as well as the invention itself, may be more fully understood from the following description, when read together with the accompanying drawings in which:

FIGS. 2A-2E are a perspective views of exemplary prosthetic ligaments in accordance with the present invention;

DESCRIPTION OF THE INVENTION

Ligament fibroblasts have the ability to regenerate ligamentous tissue if given the right physical and chemical environment in which to do so (Frank et al. (1983) *J. Orthopaed. Res.* 1:179-188). Additionally, ligament fibroblasts can migrate into a defect filled with a fibrin clot and form tissue apparently similar to ligament (Frank et al. (1983) *J. Sports Med.* 11:379-389). When an adequate matrix scaffold is present within a ligamentous defect, such ligamentous tissue may be formed. Full regeneration of an injured ligament in an otherwise healthy joint may provide normal joint motion and stability thereby preventing arthritic changes.

It has been discovered that a prosthetic ligament fabricated from short segments of fibers of biocompatible and bioresorbable polymeric connective tissue components can be surgically implanted into the knee, shoulder, or other joint so as to provide normal joint motion and stability. This prosthetic ligament also acts as a scaffold for regenerating ligamentous tissue whose ingrowth is encouraged by the physical characteristics of the implanted device.

Figure 1A:
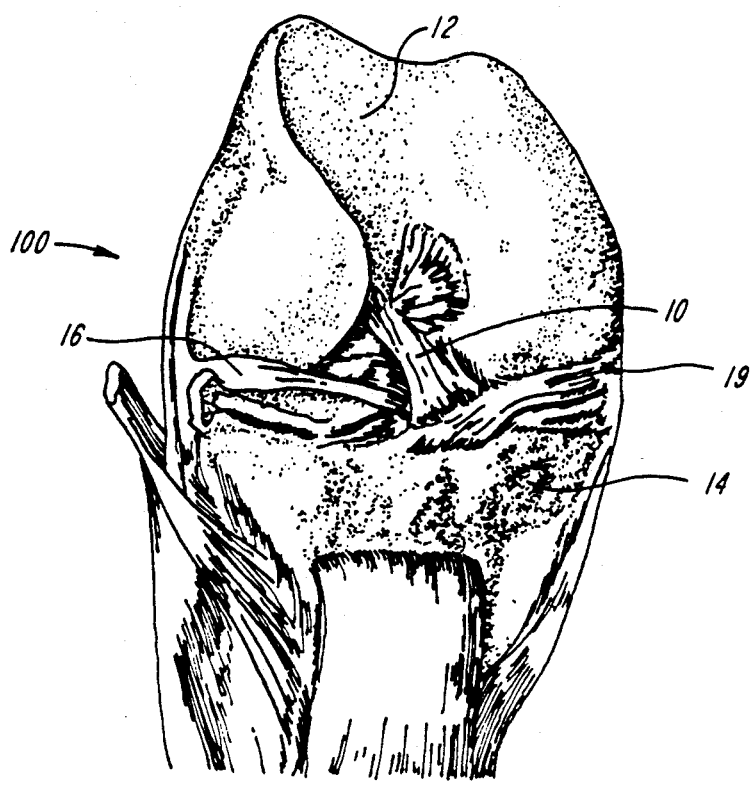
FIGS. 1A and 1B are diagrammatic representations of a human knee joint showing the normal positioning of the articular ligaments (FIG. 1A); and an articular ligament injury (FIG. 2B)
Figure 1B:
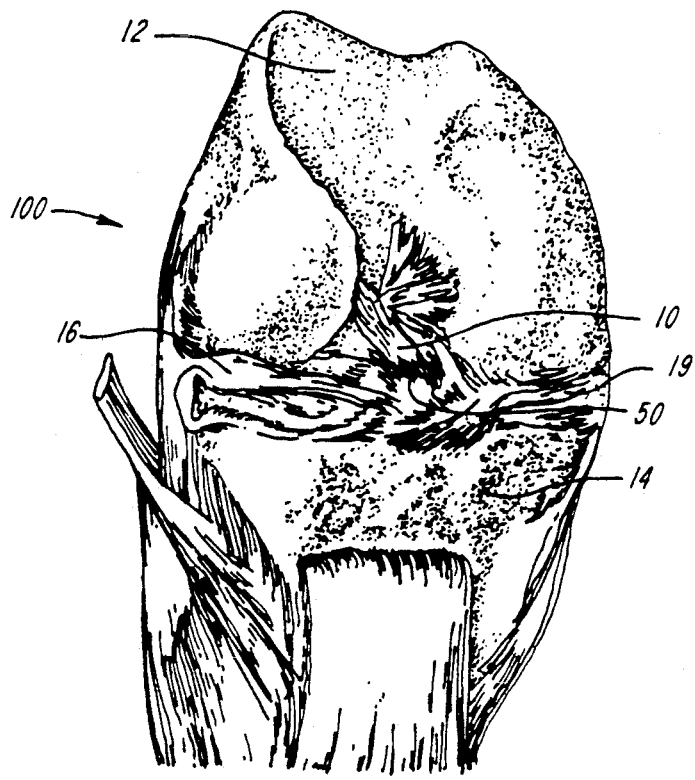

FIG. 1A shows a diagrammatic representation of the normal positioning of a native anterior cruciate ligament 10 in the human knee joint 100. This ligament connects femur 12 to tibia 14 between lateral meniscus 16 and medial meniscus 19. The prosthetic ligament of the present invention can be used to replace or enhance the functioning of such a native ligament. FIG. 1B shows a typical articular ligament injury 50 that the prosthetic ligament of the invention could be used to repair.

Figures 2A, 2C:
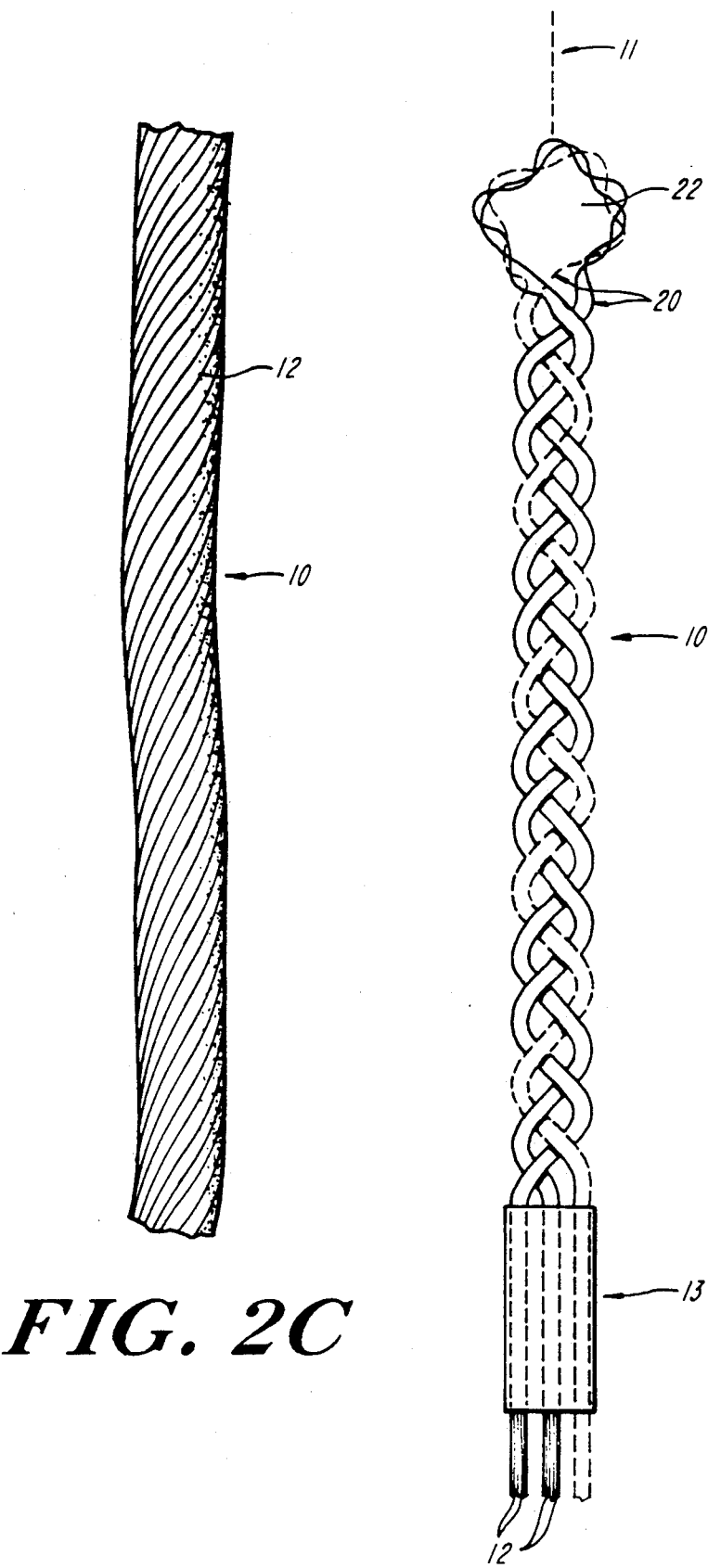
Figure 3:
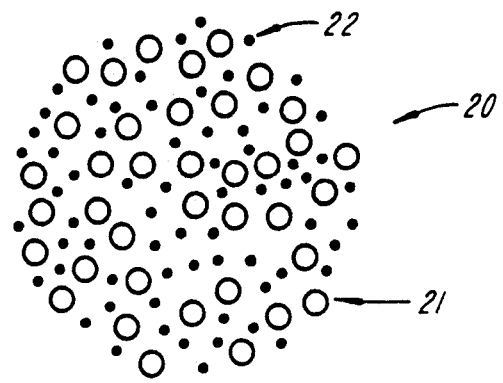
FIGS. 3 is a perspective sectional view of the prosthetic ligament of FIG. 2A.
Figure 4:
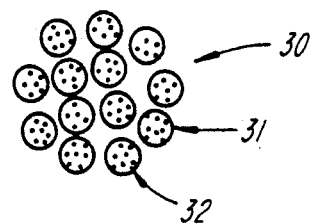
FIG. 4 is a perspective sectional view of a low density filaments of the present invention.
Figure 5:
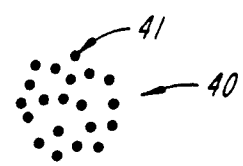
FIG. 5 is a sectional view of high density filaments of the present invention.

An exemplary prosthetic ligament 10 is shown in FIG. 2A. The prosthetic ligament 10 is generally a plurality of substantially aligned, elongated filaments 12 which extends along a central axis 11. In this embodiment, the filaments 12 have been braided or woven together about the axis 11. Brace or tube 13 holds filaments 12 together. In an alternative embodiment shown in FIG. 2C, filaments 12 have been twisted together, forming a rope-like structure. Other types of structures which include filaments aligned in a mutually adjacent relationship are also useful (FIGS. 2B, 2D, and 2E).

The prosthetic ligament may be fabricated from of any biocompatible, bioresorbable fibers of a native, synthetic, or biosynthetic polymeric connective tissue or plant connective tissue-like component. Examples of such materials include collagen, reticulin, elastin, cellulose, alginic acid, and chitosan. The following procedure may be used to prepare the type I collagen from bovine Achilles tendon.

Tendon is first cleaned of fascia and extraneous tissues and minced. The minced tendon is extracted in a 1M NaCl, pH 7.0, to remove a small portion of the collagen molecules that are newly synthesized and have not yet been incorporated into the stable fibrils, as well as glycoproteins and proteoglycans that are associated with collagen through non-covalent interactions. Other salts such as potassium chloride and the like can be used as a substitute for sodium chloride.

Lipids that are associated with the cell membranes or collagenous tissues are removed by first extracting with detergents such as Triton X-100 (Sigma Chemical Co., St. Louis, Mo.), followed by extracting with etherethanol mixtures. The concentration of Triton X-100 is usually about 2% to 4%, but is preferably about 3%. The preferred mixture of ether-ethanol is usually at about a 1:1 ratio (v/v). The period of extraction is usually from about 8 hours to about 96 hours, but is preferably from about 24 to 48 hours.

Further purification may be accomplished by extracting the tendon under acidic and basic conditions. Both acidic and basic extraction weaken the non-covalent intermolecular interactions, thus facilitating the release of non-covalently attached glycoproteins, glycosaminoglycans (GAGs), and other non-collagenous molecules.

The extraction of tendon at alkaline condition is accomplished by treating the tendon with $Ca(OH)_2$, NaOH, or the like, at a pH about 13 for a period of 8 to 96 hours in the presence of a structure-stabilizing salt such as $(NH_4)_2SO_4$, or $Na_2SO_4$ to minimize the potential risk of denaturating the collagen. Alkali treatment dissociates the non-covalently-linked glycoproteins and GAGs from the collagen matrices. The alkali also removes the residual lipid through saponification.

The acid extraction may be conducted at a PH below 3 in the presence of a structure stabilizing salt. Acids such as acetic acid, hydrochloric acid, or the like may be used. Like alkaline extraction, acid extraction removes non-covalently-linked glycoproteins and GAGs.

The non-triple helical portions of the molecule (telopeptides) are involved in intermolecular crosslinking formation. They are weak antigens and are susceptible to attack by proteases, such as pepsin and trypsin. Prolonged digestion with such proteases dissociates the fibrils into individual molecules. However, if the digestion process is properly controlled such that maximal telopeptides are removed without complete dissociation, the immunogenicity of the fibrils may be further reduced without significantly comprising the mechanical strength. For example, to isolate molecular collagen, the digestion of skin or tendon with pepsin is usually conducted at an enzyme:collagen ratio of about 1:10 (w/w) for about 24 to 96 hours at below room temperature. In comparison, fibrils may be obtained by limited pepsin digestion achieved at a ratio of about 1:100 (enzyme:collagen w/w) for about 24 to 96 hours at 4° C.

Type I collagen fibrils obtained according to this method are used to fabricate the prosthetic ligament of the present invention. However, it must be appreciated that collagen obtained from other sources, such as biosynthetically-produced collagen or analogs thereof, may also be used in the fabrication of the prosthetic ligament. These fibers may be ordered in substantially longitudinally-extending with the density of fibers being substantially uniform throughout the matrix.

The following general procedure may be used to fabricate a prosthetic ligament.

The purified connective tissue fibers are swollen in a phosphate buffered saline solution at pH 7.4. The swollen fibers are then subjected to a homogenization step to further break down the fibers to smaller fibrils without denaturing the protein. Homogenization under low shear rate is preferred, such as with a Silverson Homogenizer adapted with a disintegration head. The homogenized connective tissue is then filtered first through a 40 mesh then through a 100 mesh stainless steel screen to eliminate large fibers that have not been homogenized. The uniformly dispersed connective tissue fibrils can now be used for the production of high density and low density filaments.

One method of forming a filament includes an extrusion procedure. Briefly, a collagen or other fibril dispersion (2% to 4% w/v) is fed into a reservoir which is attached to a piston-driven device on one side and a needle at the other end such as a syringe pump device. The dispersion is pushed out through the needle through a continuous, constant piston drive to ensure a continuous, constant flow of the dispersion. The wet filaments may be extruded into a coacervation bath of acetate buffer solution, pH 4.7, in the presence of 1% NaCl. Alternatively, the wet filaments may be extruded into a salt solution bath containing 5 to 20% NaCl.

Another method of forming a filament includes placing or aggregating the dispersion into a mold form having a filamentous shape. The fibrils in the dispersion may randomly or uniformly orientated in the mold, depending on the application desired. Uniform orientation in the mold may be accomplished for example by directionally painting the dispersion into the mold with a bristled brush.

The prosthetic ligament contains porous low density filaments, and may also contain high density filaments for added strength. A typical prosthetic ligament consists of from about 10% to about 50% low density filaments having density of from about 0.05 to about 0.4 g/cm$^3$, and preferably about 0.07 to about 0.3 g/cm$^3$, and from about 50% to about 90% high density filaments having density from about 1.0 to about 1.3 g/cm$^3$.

To form low density filaments, the wet filaments are removed from the coacervation bath and freeze-dried. These freeze-dried filaments are highly porous and do not possess high tensile strength. The porosity and strength are adjusted by stretching the filaments and then subjecting the filaments to a crosslinking agent. Vapor crosslinking with formaldehyde is preferred. Alternatively, the stretched filaments may be crosslinked by dehydrothermal treatment with heat and vacuum by methods well known in the art.

High density filaments are obtained as follows. Filaments are extruded from a dispersion (2 to 4% w/v) as described above. However, after the wet filaments are collected, they are air dried under a hood to yield collagen filaments of a given diameter. The air dried filaments are subsequently crosslinked either in a solution phase using a crosslinking agent well known in the art such as glutaraldehyde, formaldehyde, and the like, or in a vapor phase also known in the art such as by exposing the filaments to formaldehyde vapor.

The filaments are then manipulated into a desired shape such as a multi-filament bundle 20 which then can be used to form a multi-filament braid of three or more bundles 20 of high density and/or low density filaments 12 (FIG. 2A), a two or more bundle helix (FIG. 2B), or a single twisted bundle (FIG. 2C) or untwisted bundle (FIG. 2D). FIG. 2E shows an embodiment 20 similar to that shown in FIG. 2D where loops 22 are formed at each end for use in fastening the prosthetic ligament in vivo.

The following procedure may be used to prepare a ligament device of braided filaments, as shown in FIG. 2A. High density and low density filaments at a ratio of 2:1 (w/w) are combined longitudinally in small bundles, having about 100 to 300 high density filaments and 50 to 150 low density filaments. Three bundles are first braided at the mid-length and then folded at the braided region to form a turn and a loop 22. The six bundles are then braided. The end of the ligament is sealed into a resorbable polymer mesh tube 13 such as a polylactate mesh tube. The thusly braided ligament can easily be stretched by 10 to 15% without strain the collagen molecules.

The crosslinked device maintains sufficient degree of hydrophilicity and elasticity which simulates the properties of the natural ligament, i.e., ability to sustain mechanical stress and to stabilize the joint. In addition, the structure provides an ideal environment for cell infiltration, extracellular matrix synthesis, and deposition resulting in regeneration of natural ligament tissue.

Polysaccharides may be dispersed throughout the fibrils in the filaments. They may act as lubricants and/or intermolecular crosslinks between fibrils. Useful polysaccharides crosslinks are composed typically of at least one of the group of molecules consisting of chondroitin 4-sulfate, chondroitin 6-sulfate, keratan sulfate, dermatan sulfate, heparan sulfate, heparin sulfate, alginic acid, chitosan and hyaluronic acid. The dispersion of polysaccharides is preferably uniform throughout the fibril dispersion and may be in the range of about 1 to 25% (weight/weight) for example.

Intermolecular crosslinkages can also be established through a dehydrothermal process (heat and vacuum) which is well known in the art. This procedure can be performed as an additional step after chemical crosslinking for added strength.

The crosslinked device has a relatively high thermal stability between about 55° to 85° C., preferably between about 65° to 75° C., for sufficient in vivo stability. This may be achieved through manipulation of the crosslinking conditions, including reagent concentration, temperature, pH and time.

By following the processes described above and in the examples set forth below, a prosthetic ligament of the forms shown in FIG. 2 may be constructed having the characteristics listed below in TABLE 1.

TABLE 1

| | |
|---|---|
| 1. Physical Characteristics | |
| a. Density (g/cm$^3$) | |
| low density filaments | 0.05–0.4 |
| high density filaments | 1.0–1.3 |
| b. Tensile Strength (Newtons) | |
| initial | 300–600 |
| after tissue ingrowth | 1000–3000 |
| c. Length (cm) | 15–17 |
| 2. Constituents | |
| a. Fibers | |
| type I or type I + type II collagen, (weight %) | 75–100 |
| b. Polysaccharides (weight %) | 0–25 |

The following non-limiting examples describe methods of fabrication and in vivo testing of the prosthetic ligament of the invention.

EXAMPLE 1

Preparation of Purified Type I Collagen

A) Tissue

Bovine, porcine or sheep Achilles tendon is obtained from USDA-approved slaughter houses. The preferred age of the animals is between 12 to 18 months. The tissue is kept cold during the purification process except where specified to minimize bacteria contamination and tissue degradation.

B) Mechanical Disintegration

The adhering tissues of carefully selected tendons are first scrapped off mechanically. The tendons are then minced or cut into fine pieces and washed in excess quantities (10 volumes) of cold water to remove residual blood proteins and water soluble materials.

C) Salt Extraction

The washed tendons are extracted in ten volumes of 5% NaCl, 0.1M phosphate buffer, pH 7.4 for 24 hours to remove salt soluble materials. The salt extracted tendons are repeatedly washed in about 10 volumes of water to remove the salt.

D) Lipid Extraction

The material is extracted in 3% Triton X-100 for 24 hours. The detergent is removed by extensive washing with water. The material is then extracted in 3 to 4 volumes of ether-ethanol (1:1 vol/vol) for 24 (±2) hours to further minimize the lipid content. The lipid extracted material is extensively washed in water to remove the ether and ethanol.

E) Acid and Base Extraction

The material is subjected to acidic and basic extractions to remove non-collagenous materials. Alkaline extraction is conducted with 3 to 4 volumes of 0.5M NaOH at pH 13 to 13.8 at room temperature in the presence of 1.0M Na$_2$SO$_4$ for 24 (±2) hours with mild agitation. Following alkaline extraction, the pH is neutralized with HCl. The pH is then adjusted to 2.5 by adding concentrated lactic acid to a final concentration of 0.2M. The acid extraction is continued for 24 (±2) hours with agitation.

F) Limited Proteolytic Digestion

The acid swollen tendon is then subjected to a limited proteolytic digestion with pepsin (enzyme:collagen=1:100 w/w) for 24 (±2) hours at 4° C. The pepsin and telopeptides are removed through dialysis.

The swollen fibrillar material is then coacervated by adjusting the pH to its isoionic point with 1M NaOH or HCl or by adjusting the ionic strength to 0.7 with NaCl. The coacervated collagen fibrils are harvested by filtration, and the filtered material extensively washed with cold distilled water. The highly purified type I collagen may be stored at −20° to −40° C. until use. Alternatively, the purified fibril dispersion may be freeze dried and stored at room temperature as dry fibrils.

EXAMPLE 2

Preparation of Low Density Filaments 15 grams of purified collagen fibrils are swollen in 500 ml phosphate buffered saline (PBS) solution to make a 3% (w/v) collagen dispersion. The swollen collagen is homogenized with a Silverson Homogenizer using a disintegration head for two minutes. The homogenized collagen is then filtered first through 40 mesh stainless steel mesh followed with a 100 mesh stainless steel filtration under vacuum. The filtered, dispersed collagen is de-aired under vacuum. The uniform collagen dispersion is fed into a syringe pump which extrudes the collagen through a modified 12 gauge needle at a rate of 1 ml per minute. The extruded collagen filaments are collected in a coacervation tank of acetate buffer pH 4.7 in the presence of 1% NaCl at 35° C. The coacervated filaments are then placed into freeze drying trays and frozen at −40° C. followed by drying at −10° C. under 150 um Hg vacuum for 24 hours. The final drying is done at 20° C. for six hours before removing the filaments from the freeze drying trays. The freeze dried collagen filaments are placed in a crosslinking chamber and crosslinked under vapor of formaldehyde generated from a 2% formaldehyde solution for 90 minutes at 95% humidity at room temperature. The crosslinked collagen filaments are stored at room temperature in a clean plastic bag until further use.

EXAMPLE 3

Preparation of High Density Filaments 15 grams of purified collagen fibrils are swollen in 500 ml phosphate buffered saline (PBS) solution to make a 3% (w/v) of collagen. The swollen collagen is homogenized with a Silverson Homogenizer using a disintegration head for two minutes. The homogenized collagen is then filtered first through 40 mesh stainless steel mesh followed with a 100 mesh stainless steel filtration under vacuum. The filtered, collagen dispersion is de-aired under vacuum. The uniform collagen dispersion is fed into a syringe pump which extrudes the collagen filaments through a modified 12 gauge needle at a rate of 1 ml per minute. The extruded wet collagen filaments are collected in a coacervation tank of acetate buffer pH 4.7 in the presence of 1% NaCl at 35° C. The coacervated collagen filaments are placed under a hood and dried by air for 24 hours. The air dried filaments are crosslinked in a 0.1% glutaraldehyde solution in a phosphate buffered saline solution, pH 7.4, for 24 hours at room temperature. The crosslinked filaments are extensively washed in water and stored at room temperature until further use.

EXAMPLE 4

Fabrication of Ligament I Device 100 to 300 high density collagen filaments and 50 to 150 low density collagen filaments (ratio of 2:1) made in accordance with EXAMPLE 2 and 3 above are combined longitudinally into small bundles for braiding. Three bundle units of 40 cm long each are first braided at the mid-point. They are subsequently folded at the mid-point to form a small loop. Six bundle units are then braided to form a composite of collagen ligament containing two thirds high density collagen fibers intertwined with one third low density porous collagen fibers. The end of the ligament is sealed into a resorbable polymer mesh tube such as polylactate mesh tube. The thusly braided ligament can easily be stretched by 10 to 15% without strain the collagen molecules. Alternatively, the braided bundles may be folded to have a loop at each end.

EXAMPLE 5

Fabrication of Ligament II Device

Same as EXAMPLE 4 except that the high density collagen filaments are substituted by polylactate monofilaments obtained from Purac America, Inc., Chicago, Ill.

EXAMPLE 6

Fabrication of Ligament III Device 15 grams of purified collagen fibrils are swollen in 500 ml phosphate buffered saline (PBS) solution, containing 0.189 g of hyaluronic acid and 0.189 g of chondroitin sulfate to make a 3% (w/v) dispersion of collagen and 0.076% (w/v) of glycosaminoglycans. The rest of the procedure is the same as EXAMPLE 2. 15 grams of purified collagen fibrils are swollen in 500 ml phosphate buffered saline solution containing 0.189 g of hyaluronic acid and 0.189 g of chondroitin sulfate to make a 3% (w/v) dispersion of collagen fibrils and 0.076% (w/v) of glycosaminoglycans. The rest of the procedure is the same as EXAMPLE 3 except that collagen filaments are crosslinked in a 1-ethyl-3-(3-dimethylaminopropyl) carbodiimide solution at pH 4.7 for 24 hours. The addition of carbodiimide is made every 3 to 4 hours, and the pH is adjusted to 4.7 after each addition of carbodiimide.

EXAMPLE 7

Description of Device Insertion

A 10 mm hole is drilled at the anatomic insertion site of the natural cruciate ligament on the femur and on the tibia. A guide suture is passed from the femur to the tibia. The guide suture is then attached to the loop at the end of the prosthetic ligament, and the ligament pulled across the joint. The ligament is fixed to the femur and the tibia by drilling a screw through the loop at the end of the ligament and into the cortical and cancellous bone. The knee is passed through a range of motion under direct visualization with either open or arthroscopic techniques. Any impinging bone is resected.

EXAMPLE 8

In Vitro and In Vivo Testing

In Vitro Testing

Each prosthetic ligament is mounted in an mechanical testing jig (MTS) with a post through each ligament end loop. The post is grasped in the mechanical jaws of the MTS force loading machine. The graft is pulled apart at a displacement rate of 15 mm/sec and compared to normal cruciate ligament strengths (estimated to be about 1500 to 2500 Newtons).

In Vivo Testing

Each Prosthetic ligament is implanted in an animal knee joint (e.g., dog, goat, monkey) and tested six months and twelve months after implantation. Following surgery the animals are allowed unrestricted cage and exercise activity for six or twelve months, at which time the animal is euthanized. Each knee is striped of extraarticular tissue. The femurs and tibias potted and loaded onto a MTS machine with the ACL aligned along the axis of the actuator. The joints are pulled apart at a displacement rate of 15 mm/sec as described by McCarthy et al. (Orthopedic Research Society Meeting, Washington, D.C. (1991).

The present invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

We claim:

1. A prosthetic ligament comprising a plurality of substantially aligned, elongated filaments,
    each of said filaments being a dry, porous, volume matrix reconstituted from biocompatible and bioresorbable fibrils, said fibrils being short segments of fibers of a polymeric connective tissue-type component, or analog thereof, at least some of said fibrils being crosslinked,
    at least one of said filaments being a high density filament having a density of about 1.0 to about 1.3 g/cm$^3$
    wherein each of said filaments establishes a bioresorbable scaffold adapted for ingrowth of ligament fibroblasts, and wherein said scaffold and said ingrown fibroblasts support natural ligament tensile forces.

2. The prosthetic ligament of claim 1, wherein said filaments comprise low density filaments having a density of about 0.05 to about 0.40 g/cm$^3$.

3. The prosthetic ligament of claim 2, wherein the density of said low density filaments is from about 0.07 to about 0.30 g/cm$^3$.

4. The prosthetic ligament of claim 1, wherein each of said fibrils are segments of a polymeric connective tissue-type component selected from the group consisting of collagen, elastin, reticulin, cellulose, alginic acid, chitosan, and analogs thereof, and mixtures thereof.

5. The prosthetic ligament of claim 4, wherein said fibrils comprise segments of collagen.

6. The prosthetic ligament of claim 1, wherein said crosslinks are formed by a chemical crosslinking reagent.

7. The prosthetic ligament of claim 6 wherein said crosslinking reagent is selected from the group consisting of glutaraldehyde, formaldehyde, carbodiimides, hexamethylene diisocyanate, bisimidates, polyglycerol polyglycidyl ether, glyoxal, adipyl chloride and mixtures thereof.

8. The prosthetic ligament of claim 7, wherein said crosslinking agent is formaldehyde.

9. The prosthetic ligament of claim 1, wherein said filaments further comprise a plurality of polysaccharide molecules interspersed with said fibrils.

10. The prosthetic ligament of claim 9, wherein at least a portion of said polysaccharide molecules provide crosslinks between ones of said fibrils.

11. The prosthetic ligament of claim 9, wherein said fibrils are present at a concentration of about 75 to 100% by dry weight, and said polysaccharide molecules are present at a concentration of about 0 to 25% by dry weight.

12. The prosthetic ligament of claim 9, wherein said polysaccharide molecules are selected from the group consisting of chondroitin 4-sulfate, chondroitin 6-sulfate, keratan sulfate, dermatan sulfate, heparan sulfate, heparin, alginic acid, chitosan, hyaluronic acid, and mixtures thereof.

13. The prosthetic ligament of claim 9, wherein polysaccharide molecules are dispersed substantially uniformly throughout said matrix.

14. The prosthetic ligament of claim 9, wherein said polysaccharide molecules are dispersed substantially non-uniformly throughout said matrix.

15. The prosthetic ligament of claim 1, wherein said fibrils are oriented in a substantially random fashion throughout said filament.

16. The prosthetic ligament of claim 1, wherein said fibrils are oriented in a substantially ordered fashion throughout said filament.

17. The prosthetic ligament of claim 1, further comprising a mesh extending from a portion of the outer surface of said filament, said mesh being resorbable and biocompatible.

18. A method of regenerating ligamentous tissue in vivo comprising the steps of:

a) providing a prosthetic ligament comprising a plurality of substantially aligned, elongated filaments in a mutually adjacent relationship, each of said filaments being a dry, porous, volume matrix reconstituted from biocompatible and bioresorbable fibrils, said fibrils being short segments of fibers of a polymeric connective tissue-type component, or analogs thereof, at least some of said fibrils being crosslinked, at least one of said filaments being a high density filament having a density of about 1.0 to about 1.3 g/cm$^3$ wherein each of said filaments establishes a bioresorbable scaffold adapted for ingrowth of ligament fibroblasts; and b) implanting said prosthetic ligament into a joint by surgical procedures, said implanted prosthetic ligament and said ingrown fibroblasts supporting normal ligament tensile forces.

19. The method of claim 18, wherein said providing step (a) comprises providing a prosthetic ligament including a plurality of polysaccharide molecules interspersed with said fibrils.

20. The method of claim 18, wherein said providing step (a) includes fabricating said prosthetic ligament, said fabricating step comprising the steps of:

(a) providing a plurality of essentially pure fibers of a polymeric connective tissue-type component selected from the group consisting of collagen, elastin, reticulin, cellulose, alginic acid, chitosan, and analogs thereof, and mixtures thereof;

(b) cutting said fibers into segments shorter than said fibers to form fibrils;

(c) aggregating said fibrils into a plurality of elongated filaments;

(d) contacting said filaments with a crosslinking reagent for a time sufficient to crosslink at least a portion of said fibrils within said filaments, whereby each filament forms a dry, porous, volume matrix adapted for the ingrowth of ligament fibroblasts; and (e) aligning a plurality of said filaments in mutually adjacent relationship, said aligned filaments forming said prosthetic ligament.

21. The method of claim 18, wherein said providing step (a) includes fabricating said prosthetic ligament, said fabricating step further comprising aggregating said fibrils with a plurality of polysaccharide molecules to form a plurality of elongated filaments.

* * * * *